US00PP36964P2

(12) United States Plant Patent
Wiens

(10) Patent No.: US PP36,964 P2
(45) Date of Patent: Sep. 16, 2025

(54) ***PETUNIA* PLANT NAMED 'WNPETSVCJ26'**

(50) Latin Name: *Petunia X hybrida*
Varietal Denomination: WNPETSVCJ26

(71) Applicant: Marc Wiens, Hackenheim (DE)

(72) Inventor: Marc Wiens, Hackenheim (DE)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 18/956,628

(22) Filed: Nov. 22, 2024

(51) Int. Cl.
*A01H 5/02* (2018.01)
*A01H 6/82* (2018.01)

(52) U.S. Cl.
USPC ..... Plt./356.17

(58) Field of Classification Search
USPC ..... Plt./356.17
CPC . A01H 5/02; A01H 5/00; A01H 6/824; A01H 6/82
See application file for complete search history.

(56) References Cited

U.S. PATENT DOCUMENTS

PP17,730 P2 * 5/2007 Sakazaki ..... A01H 6/824 Plt./356.21

* cited by examiner

*Primary Examiner* — June Hwu
(74) *Attorney, Agent, or Firm* — C. Anne Whealy

(57) ABSTRACT

A new and distinct Petunia plant named 'WNPETSVCJ26', characterized by its upright to outwardly spreading and mounding to eventually trailing plant habit; vigorous growth habit and rapid growth rate; freely branching habit; dense and bushy plant form; early and freely flowering habit; single-type flowers that are lavender in color with lighter lavender-colored throats; and excellent container and garden performance.

2 Drawing Sheets

Figure 1:
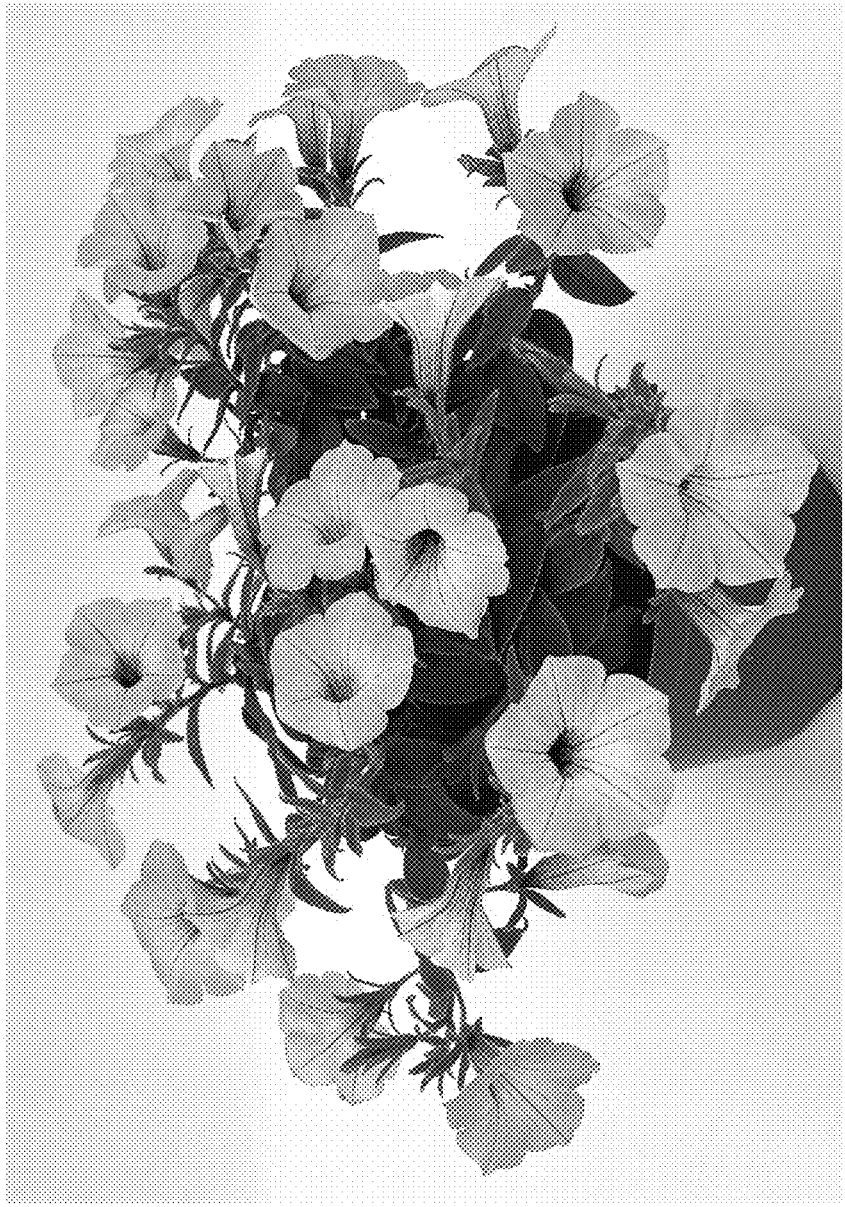

Botanical designation: *Petunia X hybrida.*
Cultivar denomination: 'WNPETSVCJ26'.

BACKGROUND OF THE INVENTION

The present invention relates to a new and distinct cultivar of Petunia plant, botanically known as *Petunia X hybrida* and hereinafter referred to by the name 'WNPETSVCJ26'.

The new Petunia plant is a naturally-occurring branch mutation of *Petunia X hybrida* 'WNPESVJAZ', disclosed in U.S. Plant Pat. No. 34,152. The new Petunia plant was discovered and selected by the Inventor on a single flowering plant from within a population of plants of 'WNPESVJAZ' in a controlled greenhouse environment in Gensingen, Germany on Aug. 19, 2022.

Asexual reproduction of the new Petunia plant by vegetative terminal cuttings in a controlled greenhouse environment in Gensingen, Germany since Aug. 22, 2022 has shown that the unique features of this new Petunia plant are stable and reproduced true to type in successive generations.

SUMMARY OF THE INVENTION

Plants of the new Petunia have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNPETSVCJ26'. These characteristics in combination distinguish 'WNPETSVCJ26' as a new and distinct Petunia plant:

1. Upright to outwardly spreading and mounding to eventually trailing plant habit.
2. Vigorous growth habit and rapid growth rate.
3. Freely branching habit; dense and bushy plant form.
4. Early and freely flowering habit.
5. Single-type flowers that are lavender in color with lighter lavender-colored throats.
6. Excellent container and garden performance.

Plants of the new Petunia can be compared to plants of the mutation parent, 'WNPESVJAZ'. In side-by-side comparisons, plants of the new Petunia differ primarily from plants of 'WNPESVJAZ' in flower color as plants of the new Petunia have flowers that are lavender in color with lighter lavender-colored throats whereas flowers of plants of 'WNPESVJAZ' are reddish purple in color. In addition, leaves of plants of the new Petunia are narrower than leaves of plants of 'WNPESVJAZ'.

Plants of the new Petunia can be compared to plants of *Petunia X hybrida* 'USTUNI6001', disclosed in U.S. Plant Pat. No. 17,730. In side-by-side comparisons, plants of the new Petunia differ primarily from plants of 'USTUNI6001' in the following characteristics:

1. Plants of the new Petunia are more outwardly spreading than and not as upright as plants of 'USTUNI6001'.
2. Plants of the new Petunia have smaller flowers than plants of 'USTUNI6001'.
3. Flowers of plants of the new Petunia are lavender in color with lighter lavender-colored throats whereas flowers of plants of 'USTUNI6001' are bright pink in color.

BRIEF DESCRIPTION OF THE PHOTOGRAPHS

The accompanying colored photographs illustrate the overall appearance of the new Petunia plant showing the colors as true as it is reasonably possible to obtain in colored reproductions of this type.

Colors in the photographs may differ slightly from the color values cited in the detailed botanical description which accurately describe the colors of the new Petunia plant.

The photograph on the first sheet (FIG. 1) is a side perspective view of a typical flowering plant of 'WNPETSVCJ26' grown in a container.

Figure 2:
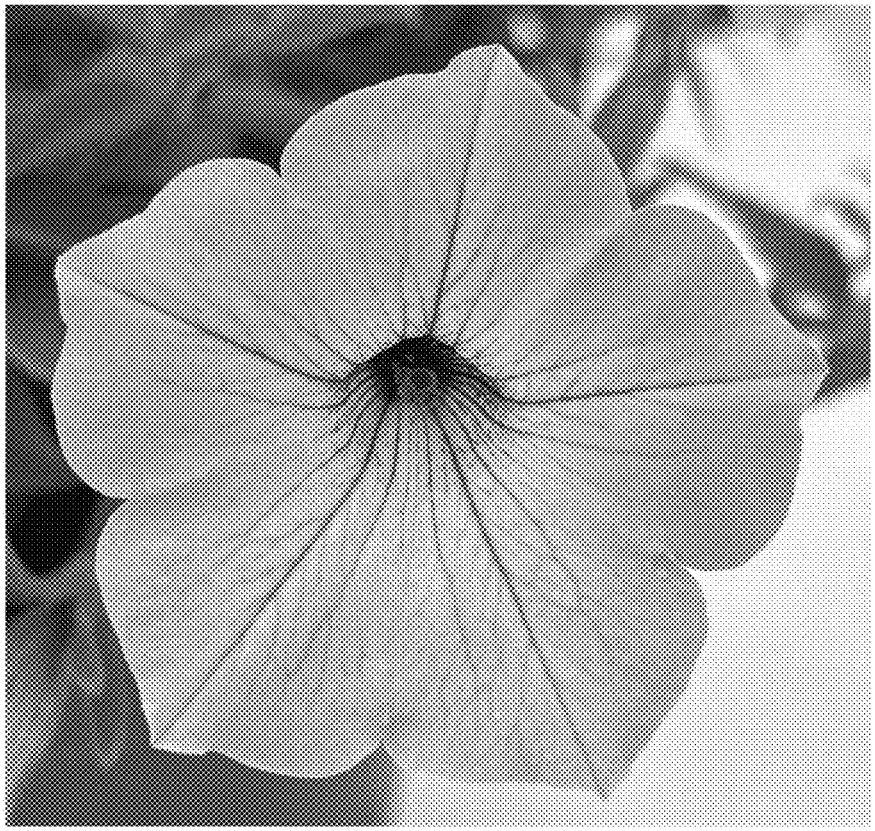

The photograph on the second sheet (FIG. 2) is a close-up view of a typical flower of 'WNPETSVCJ26'.

DETAILED BOTANICAL DESCRIPTION

The aforementioned photographs and following observations and measurements describe plants grown during the late summer to early autumn in 813 ml containers in a glass-covered greenhouse in Loudon, New Hampshire and under cultural practices typical of commercial Petunia production. During the production of the plants, day temperatures ranged from 18° C. to 20° C. and night temperatures ranged from 16° C. to 18° C. Plants were pinched one time and were eight weeks from planting rooted young plants when the photographs and description were taken.

In the following description, color references are made to The Royal Horticultural Society Colour Chart, 2015 Edition, except where general terms of ordinary dictionary significance are used.

Botanical classification: *Petunia X hybrida* 'WNPETSVCJ26'.

Parentage: Naturally-occurring branch mutation of *Petunia X hybrida* 'WNPESVJAZ', disclosed in U.S. Plant Pat. No. 34,152.

Propagation:

- *Type*.—Terminal vegetative cuttings.
- *Time to initiate roots, summer*.—About three to four days at ambient temperatures ranging from 17° C. to 29° C.
- *Time to initiate roots, winter*.—About five to seven days at ambient temperatures ranging from 17° C. to 21° C.
- *Time to produce a rooted plant, summer*.—About three weeks at ambient temperatures ranging from 17° C. to 29° C.
- *Time to produce a rooted plant, winter*.—About four weeks at ambient temperatures ranging from 17° C. to 21° C.
- *Root description*.—Medium in thickness, fibrous; typically white in color, actual color of the roots is dependent on substrate composition, water quality, fertilizer type and formulation, substrate temperature and physiological age of roots.
- *Rooting habit*.—Freely branching; medium density.

Plant description:

- *Plant and growth habit*.—Relatively compact, upright to somewhat outwardly spreading and mounding to eventually trailing plant habit; freely branching habit with five to seven primary lateral branches with secondary laterals developing potentially at every node, dense and bushy plant form; pinching enhances development of lateral branches; vigorous growth habit and rapid growth rate.
- *Plant height*.—About 14 cm to 16 cm.
- *Plant diameter* (*area of spread*).—About 34 cm to 40 cm.
- *Lateral branches*.—Length: About 17 cm to 18 cm. Diameter: About 3 mm. Internode length: About 1 cm to 1.2 cm. Strength: Strong; flexible, not brittle. Aspect: Initially upright then outwardly spreading to eventually trailing. Texture and luster: Densely pubescent; pubescence, fine; moderately glossy. Color, developing and developed: Close to 146A.

Leaf description:

- *Arrangement*.—Alternate before flowering; opposite after flowers develop; leaves simple.
- *Length*.—About 4.2 cm to 4.75 cm.
- *Width*.—About 2 cm to 2.25 cm.
- *Shape*.—Ovate to elliptic.
- *Apex*.—Acute.
- *Base*.—Cuneate to obtuse.
- *Margin*.—Entire, slightly undulate.
- *Texture and luster, upper and lower surfaces*.—Moderately pubescent, pubescence, minute; slightly glossy.
- *Venation pattern*.—Pinnate, arcuate.
- *Color*.—Developing leaves, upper and lower surfaces: Close to 146A. Fully developed leaves, upper surface: Close to 146A; venation, close to 146A. Fully developed leaves, lower surface: Close to 146A to 146B; venation, close to 144A to 144B.
- *Petioles*.—Length: About 5 mm to 7 mm. Diameter: About 2 mm to 3 mm. Strength: Moderately strong, flexible. Texture and luster, upper and lower surfaces: Moderately pubescent; slightly glossy. Color, upper surface: Close to 144A. Color, lower surface: Close to 144B.

Flower description:

- *Flower type and flowering habit*.—Single terminal and axillary salverform flowers; flowers face mostly upward to outwardly; freely flowering habit with about 120 to 160 developing flowers and open flowers per plant during the flowering season.
- *Natural flowering season*.—Long day responsive; long flowering period, plants flower from early spring until frost in the autumn, flowering continuous during this period; early flowering habit, depending on temperature, plants begin flowering about five to seven weeks after planting rooted young plants.
- *Flower longevity on the plant*.—Depending on temperature, about one to two weeks; petals not persistent, and sepals, persistent.
- *Fragrance*.—None detected.
- *Flower buds, before showing petal color*.—Length: About 1.25 cm. Diameter: About 3.5 mm to 4 mm. Shape: Oblong, elongate. Texture and luster: Pubescent; slightly glossy. Color, developing sepals: Close to 144A.
- *Flower diameter*.—About 4 cm to 4.2 cm.
- *Flower depth* (*height*).—About 3.3 cm to 3.5 cm.
- *Throat diameter*.—About 8 mm.
- *Tube length*.—About 2.2 cm to 2.4 cm.
- *Tube diameter, distally*.—About 9 mm.
- *Tube diameter, proximally*.—About 2 mm to 2.5 mm.
- *Petals*.—Quantity and arrangement: Five petals fused in a single salverform whorl. Petal lobe length (from throat): About 1.75 cm to 1.8 cm. Petal lobe width: About 1.75 cm. Petal lobe shape: Roughly spatulate.

Petal lobe apex: Cuspidate. Petal lobe margin: Entire; slightly undulate. Petal lobe texture and luster, upper surface: Smooth, glabrous; velvety; matte. Petal lobe texture and luster, lower surface: Smooth, glabrous; matte. Throat texture and luster: Smooth, glabrous; slightly glossy. Tube texture and luster: Moderately pubescent; matte. Color: When opening and fully opened, upper surface: Close to N75A; towards the throat, close to 76A to 76B; venation, close to 79A to 79B; color becoming closer to N75A to N75B with subsequent development. When opening and fully opened, lower surface: Close to 76B to 76C; venation, close to 79A to 79B; color becoming closer to 76C with subsequent development. Flower throat (inside): Close to 76B to 76C; venation, close to 79A to 79B. Flower tube (outside): Close to 76B to 76C; venation, close to 79A to 79B.

*Sepals*.—Quantity and arrangement: Five sepals fused in a single star-shaped whorl; sepals flaring outwardly. Calyx length: About 1.4 cm to 1.5 cm. Calyx diameter: About 5 mm to 6 mm. Length: About 1.4 cm to 1.5 cm. Width: About 2 mm to 2.5 mm. Shape: Narrowly lanceolate to linear. Apex: Acute. Margin: Entire. Texture and luster, upper and lower surfaces: Moderately pubescent; pubescence, fine; slightly glossy. Color, upper and lower surfaces: Close to 144A.

*Peduncles*.—Length: About 1.75 cm. Width: About 1 mm to 1.5 mm. Strength: Moderately strong; wiry and flexible, not brittle. Angle: About 45° to 90° from the stem axis. Texture and luster: Densely pubescent; slightly glossy. Color: Close to 144A.

*Reproductive organs*.—Stamens: Quantity per flower: About five. Filament length: About 1.7 cm to 1.8 cm. Filament color: Close to 76C to 76D. Anther length: About 1 mm. Anther shape: Bi-lobed. Anther color: Close to 94B. Pollen amount: None observed. Pistils: Quantity per flower: One. Pistil length: About 1.5 cm to 1.75 cm. Style length: About 1.4 cm to 1.6 cm. Style color: Proximally, close to 144C to 144D, and distally, close to 79A. Stigma diameter: About 1.5 mm to 2 mm. Stigma shape: Round. Stigma color: Close to 79A. Ovary color: Close to 144A.

*Seeds and fruits*.—To date, seed and fruit development has not been observed on plants of the new Petunia.

Pathogen & pest resistance: To date, plants of the new Petunia have not been noted to be resistant to pathogens or pests common to Petunia plants.

Garden performance:

Plants of the new Petunia have been observed to have excellent garden performance and have been observed to tolerate rain, wind and temperatures ranging from about 5° C. to about 40° C.

It is claimed:

1. A new and distinct Petunia plant named 'WNPETSVCJ26' as herein illustrated and described.

* * * * *